United States Patent [19]

Ouellette et al.

[11] Patent Number: 4,644,174
[45] Date of Patent: Feb. 17, 1987

[54] APPARATUS FOR ANALYZING THE FORMATION OF A PAPER WEB

[75] Inventors: Roland J. Ouellette; Peter W. Hodgson, both of Hawkesbury; Roland J. Trepanier, L'Orignal, all of Canada

[73] Assignee: CIP Inc., Canada

[21] Appl. No.: 775,973

[22] Filed: Sep. 13, 1985

[30] Foreign Application Priority Data

May 16, 1985 [CA] Canada .................. 481705

[51] Int. Cl.[4] ........................................... G01N 21/89
[52] U.S. Cl. .................................. 250/559; 250/572; 356/430; 162/198
[58] Field of Search ...................... 250/559, 571, 572; 356/431, 430; 162/198

[56] References Cited

U.S. PATENT DOCUMENTS

| | | | |
|---|---|---|---|
| 3,114,791 | 12/1963 | Zabel et al. | 88/14 |
| 3,135,867 | 1/1985 | Daneff | 356/431 |
| 3,469,104 | 10/1985 | Hector | 250/559 |
| 3,525,871 | 10/1985 | Lehtinen | 356/430 |
| 3,534,402 | 11/1985 | Crowell et al. | 250/571 |
| 3,639,768 | 2/1972 | Mancini | 250/205 |
| 3,992,100 | 11/1976 | Lodzinski | 356/73 |
| 4,019,066 | 4/1977 | Lucas | 250/562 |

OTHER PUBLICATIONS

Burkhard et al., "A Formation Tester which Graphically Records Paper Structure", Pulp & Paper Magazine of Canada, p. T319, Jun. 1960.

Primary Examiner—David C. Nelms
Assistant Examiner—Charles Wieland
Attorney, Agent, or Firm—Sughrue, Mion, Zinn, Macpeak and Seas

[57] ABSTRACT

On-line apparatus for analyzing the formation of a moving web of paper, using a source of light directing a beam through the paper and a photodetector receiving the light which has passed through the paper, has a circuit preferably including a tunable band pass filter and demodulator producing a D.C. output reflecting size and distribution of flocs. The output gives similar results to those obtained by visual judgement of formation.

2 Claims, 10 Drawing Figures

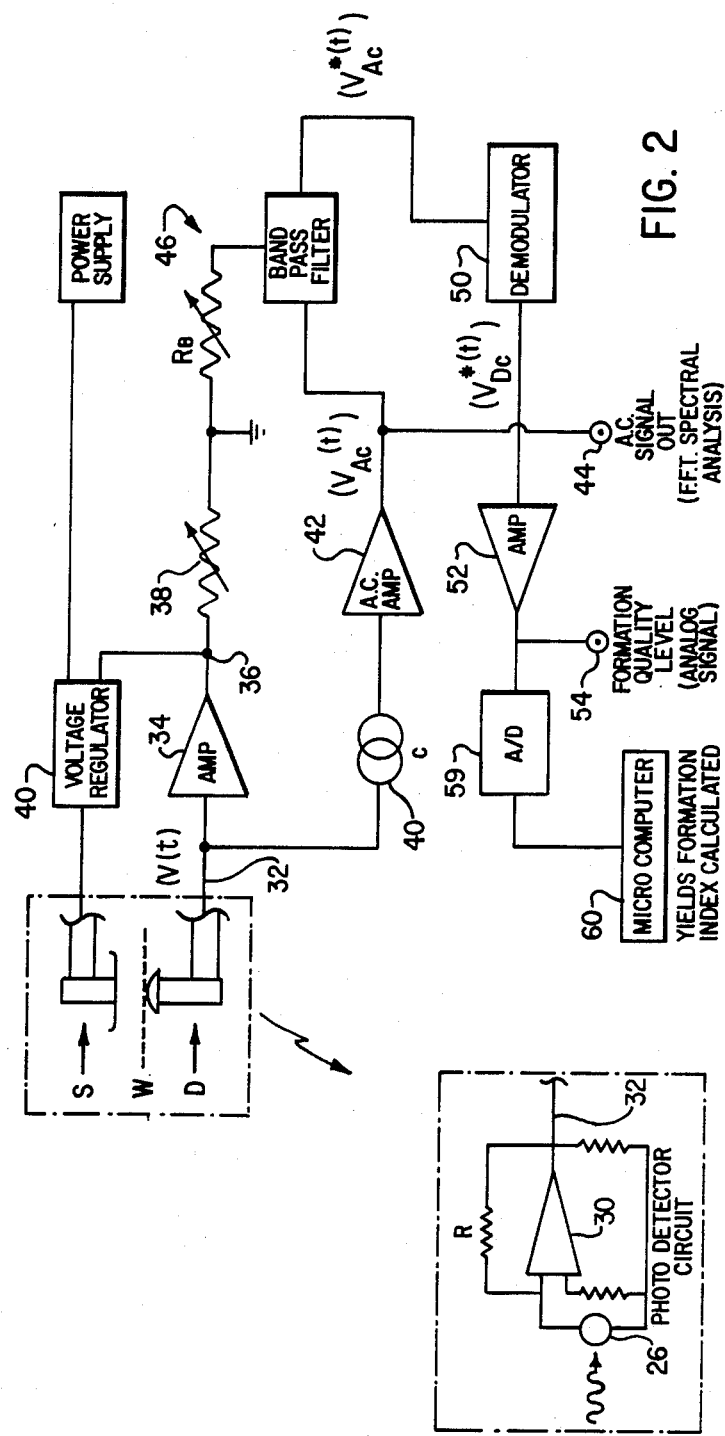

APPARATUS FOR ANALYZING THE FORMATION OF A PAPER WEB

BACKGROUND OF THE INVENTION

This invention relates to apparatus capable of continuously measuring the formation of paper while it is being produced by a papermaking machine.

The term "formation", as applied to paper, means the relative uniformity of distribution of fibres in the paper sheet. Nonuniformity, or poor formation, commonly arises because flocculation occurs in the fibre suspension from which the paper is made. This flocculation may occur prior to the delivery of the suspension to the drainage section of the paper machine or in the drainage section itself, and in either case results in poor formation. Formation depends on complex interactions of equipment, fiber and paper making parameters. Formation nonuniformity occurs as variations in mass per unit area over a relatively narrow range of distances commonly accepted to be within 0.1 to 10 cm. The term "floc" is used to denote a small area of mass per unit area above the average for the web. The characterization of formation therefore requires data concerning the relative size and spatial distribution of the flocs in a sheet of paper as well as the nonuniformities in weight distribution resulting from equipment related effects such as nonuniform distribution of flow to the fluid removal section of the machines.

Formation is an important parameter of paper quality since it affects many end use performance characteristics. For example variations of mass distribution of the dimensions of formation (i.e. 0.1–10 cm) interact with the calendering process to produce variations of density of the same dimensions. This can seriously affect printing quality in certain processes such as gravure printing where a high print gloss is desirable. Good formation produces uniform sheet density and uniform print gloss while poor formation produces nonuniform sheet density and an undesirable print mottle.

The traditional technique of judging formation has been by visual examination of samples in transmitted light by an experienced observer. This is capable of general comparisons of a limited number of samples but does not produce numerical results. It is also vulnerable to differences between observers and with time. Instruments that measure formation and produce numerical results are in existence. Most, however, are off machine units that measure a sample of paper remote from the paper machine. While this is a valuable method it does have limitations. Formation is a dynamic characteristic that can vary with subtle changes in the forming section. Measurements with an off machine instrument are limited to the end of the reel or require the loss of considerable paper to get to samples within a reel. These limitations are eliminated if the formation measurement is carried out on the machine in real time. In that way cause and effect can be closely associated.

The basic principal of most if not all formation instruments is the measurement of the attenuation of a beam of light as it is transmitted through the web. This beam scans the sheet and produces a signal proportional to the weight of the sheet that is characteristic of the formation. The differences between instruments lie in the technique of scanning the sheet and in obtaining a usable index of formation from the very complex signal obtained from the sensor. In off machine instruments some mechanical scanning device is provided. For on machine instruments the motion of the paper through the machine provides part of the scanning facility. The sensor may remain stationary on the machine and produce a reading alone one line in the machine direction of the paper or it may be mounted on a scanning device which reciprocates across the width of the web. This produces a measurement that covers both the length and width of the paper being processed.

U.S. Pat. Nos. 3,114,791, which issued Dec. 17, 1963 to Zabel, et al. and 3,525,871, which issued Aug. 25, 1970 to Lehtinen, represent examples of on line formation analysers. The Zabel patent uses two phototubes which serve as sensing elements of a scanning device, these being spaced apart to sense different areas. The net signal derived from the phototubes is a differential signal representing the difference in light intensity on the phototubes at any given instant in time. The Lehtinen patent describes a feedback system which compensates for overall changes in the light transmittance of the paper.

SUMMARY OF THE INVENTION

The formation quality of a moving sheet is determined from the variations in transmitted light which are sensed by a photodetector after passing through the sheet. The photodetector's signal is processed electronically to remove the long term components and retain the short term (0.1 to 10 cm length) components used in the formation quality determination. This AC signal is sent through a filter which passes those frequencies associated with formation. This effect can be achieved with an electronic filter or by statistical manipulation of the digitized data. This conditioned AC signal is then amplitude demodulated to produce a voltage output signal whose level is a function of the peak to peak amplitude of the conditioned AC signal. Thus, the post amplitude demodulated signal is dependent on the magnitude of the small scale grammage variations as well as their spatial distribution in the plane of the sheet. Furthermore this output signal is independent of the speed of the moving sheet. Any long term changes in the sheet's average weight, which are not formation by definition of dimension, are rejected by the filter. Similarly the effects of ageing and cleanliness of the optical system are eliminated.

BRIEF DESCRIPTION OF THE DRAWINGS

FIG. 2 is a circuit diagram of the apparatus as a whole;

FIG. 2a is a circuit diagram of the photodetector circuit;

DESCRIPTION OF THE PREFERRED EMBODIMENT

Figure 1:
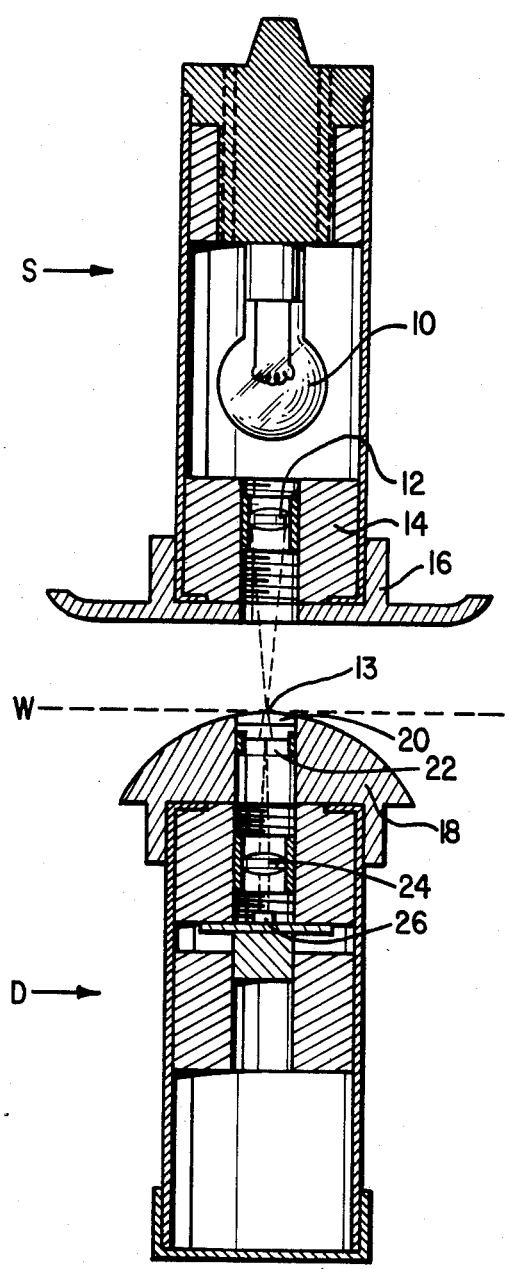
FIG. 1 is a sectional elevation through the light source/photodetector elements of the apparatus.

FIG. 1 shows details of a light source and a detector D arranged on opposite sides of a moving paper web W leaving the forming section of a paper-making machine. The light for source D is provided by an incandescent bulb 10 maintained at a selected voltage between 6 V dc and 16 V dc. A condensing lens 12 focuses a spot of light 13 on the paper web. The focal length of the lens 12 is chosen to be longer than the distance between the web and the center of the lens so that the spot size may be changed from 0.1 cm to 1.0 cm in diameter by raising or lowering the lens in its housing 14. The web W passes between ski 16 attached to source S and a ski 18 attached to detector D, and comes in contact with the detector ski 18. The light spot 13 is transmitted and scattered through the web and then passes through a 2 mm thick acrylic window 20 in detector D to an aperture 22. The diameter of this aperture is made to coincide with the size of light spot 13 and thus ranges between 0.1 cm and 1.0 cm. Light from the aperture is refocussed by a detector condensing lens 24 onto a 2 mm wide photodiode 26 whose signal is preamplified before being sent to the electronic circuit illustrated in FIG. 2.

FIG. 2 shows, diagrammatically, the light source S, the paper web W, and detector D, in addition to the circuit components which amplify and analyse the signals from the detector. FIG. 2a shows details of the photodetector circuit.

The photo-diode 26 of the detector has a resistance $R_D$ which is a function of the light intensity $h\nu$ passing through the web. A change in $R_D$ results in a gain change in a pre-amplifier 30 causing a change in the output voltage at 32. This photodetector circuit is temperature stable making it suitable for a mill environment. It includes a resistance R in parallel with the pre-amplifier 30.

It can be shown that the amplified voltage at 32, at any instant, only varies with the instantaneous transmittance of the web. More specifically, $$V(t) = RKIT(t)$$

where

Figure 3A:
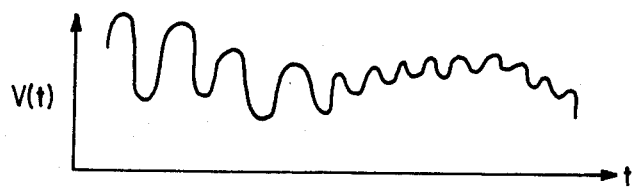
FIG. 3 is a representation of the wave forms at different stages in the processing of the signal from the detector, the different stages being shown at FIGS. 3A to 3F.

V(t) is the amplified voltage at 32 at any instant;
R is the value of resistance R;
K is a constant;
I is the intensity of light from source S; and
T(t) is the instantaneous transmittance of the web W.
A sample plot of V(t) is shown in FIG. 3A.

The instantaneous voltage V(t) can be considered as a short term AC variation $V_{AC}(t)$, depending on formation, riding on a long term, D.C., pedestal ($V_{DC}$) which is dependent for example on relatively long term basis weight changes in the paper or dust particles in the optical pathway. Thus:

$$V(t) = V_{AC}(t) + V_{DC}$$

A first part of the circuit shown uses the long term, D.C. component to regulate the light source and to minimize the longer term variations. This is accomplished by passing the voltage signal at 32 through a high stability amplifier 34 which has a 30 db gain and an adjustable voltage outlet at 36. The highest frequency response is set by an adjustable resistive network 38, having resistance $R_L$, which determines the circuit time constant. In order to eliminate long term variations in opacity such as changes in the web basis weight or the accumulation of dirt in the optical pathway which are not classified as formation, i.e. those occurring at intervals of 50 cm or longer, the time constant is chosen as:

Time Const. = 0.50 m/web speed, m/s

Once set, the voltage at 36 sends a signal to a voltage regulator 40 which controls the intensity of light source S. In addition to minimizing long term variations, this automatic light control also protects the photodetector by reducing the light intensity should there be a web break.

Figure 3B:
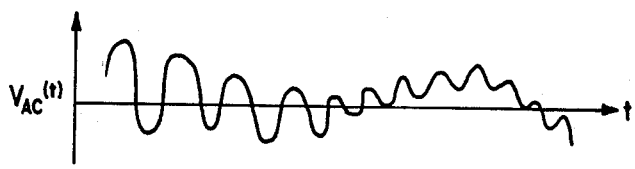

A second part of the circuit analyses the AC component of the signal at 32 and provides an output dependent on paper formation. For this purpose the voltage signal at 32 is decoupled at capacitor 40 and sent to an A.C. coupled amplifier 42. This amplifier has a flat response from 20 Hz to 100 kHz. The output signal from this amplifier, which is illustrated at FIG. 3B as $V_{AC}(t)$ is directed along 2 paths: one directly goes to an output 44 and is suitable for Fast Fourier Transform (FFT) Spectral Analysis; the other leads to a tunable band pass filter (TBPF) 46. This TBPF has a center frequency which is set to give a maximum response at a floc wavelength of 3 cm. (0.03 m). The TBPF center frequency is tuned according to:

$$\text{TBPF center frequency (Hz)} = \frac{\text{Web Speed (m/s)}}{0.03}$$

Figure 3C:
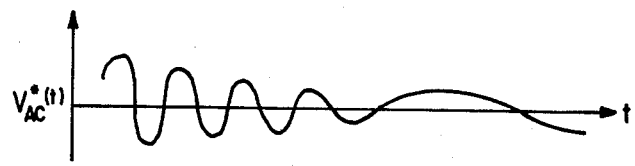

Thus a web speed of 1000 m/min (16.7 m/sec) yields a center frequency of 555.6 Hz. The TBPF is tuned by a variable potentiometer having a resistance $R_B$. This gives an A.C. signal ($V^*_{AC}(t)$) the amplitude of which is dependent on formation; this is illustrated in FIG. 3C.

Figure 4:
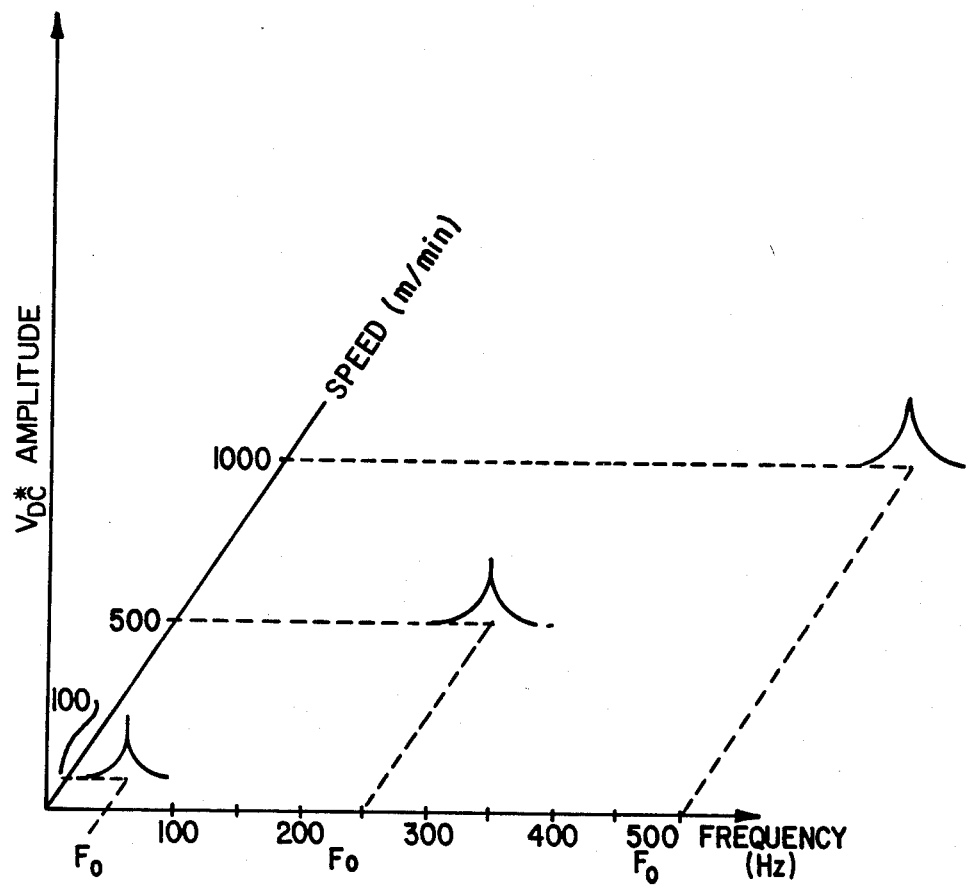
FIG. 4 is a diagram showing variation of tunable band pass filter frequencies with web speed.

FIG. 4 illustrates the relation between the centre frequency $F_o$ and band width of the TBPF and web speed, and shows for example the centre frequencies and band widths for web speeds of 100 m/min, 500 m/min, and 1000 m/min. Analysis shows that at all web speeds the input signals caused by floc wavelengths of less than 2.3 cm and greater than 3.7 cm are are attenuated to 10% of the signal corresponding to a wavelength of 3.0 cm; i.e. such wavelengths are largely eliminated by the TBPF.

Figure 3D:
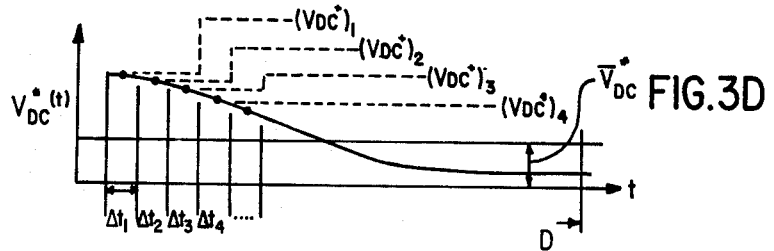

The A.C. voltage signal from 46 is processed through a demodulator circuit 50 which consists of a half wave rectifier followed by a capacitor filter. The output is a D.C. voltage level which is directly proportional to the peak to peak amplitude of the incoming A.C. voltage signal. The dependence of this D.C. output on the incoming A.C. signal is modified by the tandem arrangement of the TBPF and the demodulator 50. Thus, the D.C. output may be represented by:

$$V^*_{DC}(t) = [A(f) \times V_{AC}(t)]$$

where:
A(f) = TBPF frequency dependent amplification;
$V_{AC}(t)$ = the decoupled A.C. voltage signal at 42
The quantity $V^*_{DC}(t)$ is illustrated in FIG. 3D.
This D.C. output is a function of the paper transmission coefficients, as follows:

$$V^*_{DC}(t) = C(f)|T(t) - \overline{T}|$$

where C(f) represent constant terms, and $\overline{T}$ is the time average transmittance of paper. At any instant, $V^*_{DC}(t)$ is a measure of the formation quality. Further amplification by amplifier 52 makes the signal suitable for analog processing at 54, or digital processing by micro computer 60 which is connected to amplifier 52 via an analog to digital converter circuit 59.

An on-line formation index F can be derived which is dependent both on floc size distribution and the optical density variations of the sheet formation. This index is the sum of the time averaged digitized signal, $\overline{V}^*_{DC}$, and the absolute value of the signal's standard devication, $\sigma_{DC}$:

$$F = \overline{V}^*_{DC} + |\sigma_{DC}|$$

where, $$\overline{V}^*_{DC} = \frac{1}{D} \sum_{i=0}^{D} (V^*_{DC})_i$$

$$|\sigma_{DC}| = \left[ \frac{1}{D} \sum_{i=0}^{D} [(V^*_{DC})_i - \overline{V}^*_{DC}]^2 \right]^{\frac{1}{2}}$$

where:

D is the numer of measurements over a time interval $\Delta T$, $(V^*_{DC})_i$ is the digitized voltage measured during $\Delta t_i$, $\Delta t_i$ is a short interval of time determined by the A/D conversion process.

Figure 3E:
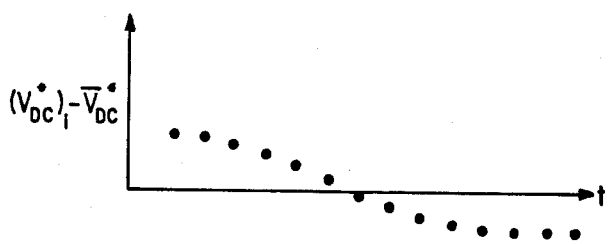
Figure 3F:
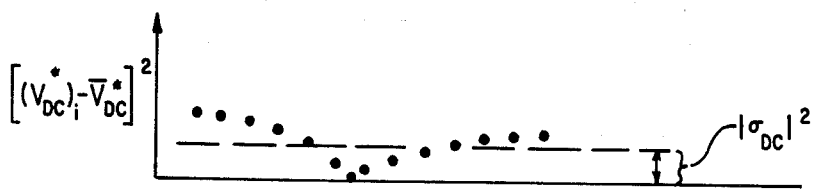

FIG. 3D illustrates the time averaged signal $\overline{V}^*_{DC}(t)$ and the quantities $\Delta t_i$ and $(V^*_{DC})_i$. FIG. 3E shows the expression $[(V^*_{DC})_i - \overline{V}^*_{DC}]$, i.e. the deviation of the signal from its average, and FIG. 3F shows the absolute value of the deviation in terms of $[(V^*_{DC})_i - \overline{V}^*_{DC}]^2$. FIG. 3F also shows the square of the standard deviation $|\sigma_{DC}|$ derived from this latter term. The formation index is produced by the micro computer 60 which averages the signal received from the A/D converter 59, computes the absolute value of the standard deviation $|\sigma_{DC}|$, and continually computes the formation index by adding these signals. The formation index produced in this way is found to agree well, in terms of ranking, with visual inspection of paper by a panel of experts.

It has been found that the TBPF is particularly useful in removing from the signal the effect of floc sizes smaller or larger than these considered to be formation and that have tended to unduly influence the results obtained with prior art devices. The formation index is a calculated function produced from the variation of the signal passed by the TBPF. This index has been found to closely agree with visual judgement obtained in the traditional way.

Instead of using the TBPF 46 and the demodulator 50, the signal from the amplifier 42 can be fed directly to an analog to digital converter circuit which has numerical filter means to remove frequencies unrelated to paper formation, and numerical demodulator means, in addition to the functions of the previously described micro-computer 60.

We claim:

1. On-line apparatus for analysing the relative uniformity of fiber distribution of a moving web of paper comprising:
   (a) a source of light which in operation directs a narrow beam of light onto the moving web,
   (b) a detector positioned so as to receive the beam of light after it has passed through the web and having photodetector means,
   (c) a circuit connected to the photodetector means and having amplifier means connected to receive decoupled A.C. signals from the photodetector means, a tunable band pass filter connected to the output from said amplifier means, a demodulator connected to receive signals from the tunable band pass filter and indicator means connected to the output from the demodulator, said tunable band pass filter being tuned, in relation to the web speed, to give a maximum response at a floc wavelength of around 3 cm. and being arranged to attenuate floc wavelengths of less than 2.3 cm. or more than 3.7 cm. to about 10% of said maximum response, wherein said indicator means includes an analog to digital converter circuit, means for averaging the signal received from said converter circuit, means for computing the standard deviation of said digitized signal, and means for continually computing a formation index which is the sum of said time averaged digitized signal and the absolute value of said standard deviation.

2. Apparatus according to claim 1, wherein there is provided an adjustable resistance in a network which receives a signal derived from the photodetector means and having a time constant consistent with long term variations in transmittance of the sheet, and a voltage regulator connected to said resistive network and operative to adjust the intensity of said light source so as to minimize the effect of such long term variations in the signals provided by the photodetector means.

* * * * *